(12) United States Patent
Guillou et al.

(10) Patent No.: US 9,127,139 B2
(45) Date of Patent: Sep. 8, 2015

(54) PROCESS FOR LABELING MATERIALS BASED ON ORGANIC THERMOPLASTIC OR THERMOSETTING POLYMER MATRICES

(75) Inventors: Olivier Guillou, Cesson-Sevigne (FR); Carole Daiguebonne, Cesson-Sevigne (FR); Nicolas Kerbellec, Pontivy (FR)

(73) Assignee: INSTITUT NATIONAL DES SCIENCES APPLIQUEES DE RENNES (FR)

( * ) Notice: Subject to any disclaimer, the term of this patent is extended or adjusted under 35 U.S.C. 154(b) by 188 days.

(21) Appl. No.: 12/602,864

(22) PCT Filed: Jun. 4, 2008

(86) PCT No.: PCT/EP2008/056904
§ 371 (c)(1),
(2), (4) Date: Apr. 16, 2010

(87) PCT Pub. No.: WO2008/148792
PCT Pub. Date: Dec. 11, 2008

(65) Prior Publication Data
US 2010/0207067 A1 Aug. 19, 2010

(30) Foreign Application Priority Data

Jun. 6, 2007 (FR) ..................................... 07 04024

(51) Int. Cl.
*C09K 11/06* (2006.01)
*C09K 11/02* (2006.01)
(Continued)

(52) U.S. Cl.
CPC ................. *C08K 5/098* (2013.01); *C09K 11/02* (2013.01); *C09K 11/06* (2013.01); *C09K 2211/182* (2013.01); *G01N 2021/1746* (2013.01); *Y10S 252/965* (2013.01)

(58) Field of Classification Search
CPC ............... C09K 11/77; C09K 11/7783; C09K 11/7766; C09K 11/06; C09K 11/02; C09K 11/025; C09K 11/65; C09K 2211/182; A61K 49/06; A61K 49/08; A61K 49/0013–49/0021; A61K 49/0085; A61K 49/0093; C09D 5/22; C09D 11/50; B41M 3/144; G21K 4/00; H01L 51/5012; H05B 33/14; C08K 5/0091; C08K 5/098; G01N 2021/1746; G01N 21/33; G01N 21/35; G01N 21/6428; G01N 21/6439; G01N 21/6441; G01J 1/58; Y10S 252/965
USPC ........ 252/301.16, 301.34, 301.35; 106/31.15, 106/31.32, 31.64; 534/15, 16
See application file for complete search history.

(56) References Cited

U.S. PATENT DOCUMENTS 4,572,803 A * 2/1986 Yamazoe et al. ................. 534/16
6,344,360 B1 * 2/2002 Colvin et al. ................... 436/94
(Continued)

FOREIGN PATENT DOCUMENTS

EP        1914289 B1 * 12/2009
WO    WO 2004/052979     6/2004

OTHER PUBLICATIONS

Cai et al., 'Controlled Assembly of Dinuclear Metallorings into 1D Coordination Polymer and Mixed-metal Rare Earth Complexes with Red-to-Green Luminescence Properties', 2004, Chemistry Letters, vol. 33, pp. 342-343.*

(Continued)

*Primary Examiner* — Matthew E. Hoban
*Assistant Examiner* — Lynne Edmondson
(74) *Attorney, Agent, or Firm* — Thomas Horstemeyer, LLP (57) ABSTRACT

Process for labelling a material based on at least one organic thermoplastic or thermosetting polymer matrix comprising a step that consists in incorporating therein, by dispersion during its manufacture or its formation, at least one compound based on at least one photoluminescent rare earth in a concentration that renders this compound detectable under UV irradiation, said compound being a coordination polymer that is in the form of a crystallite obtained by reaction of at least one photoluminescent rare-earth ion with at least one unsaturated organic ligand.

13 Claims, 7 Drawing Sheets

Light spectra of compounds $Ln_2(C_8O_4H_2)_3(H_2O)_4$
with Ln = Dy, Tb or Eu (51) Int. Cl.
*G01J 1/58* (2006.01)
*G01N 21/64* (2006.01)
*C08K 5/098* (2006.01)
*G01N 21/17* (2006.01)

(56) References Cited

U.S. PATENT DOCUMENTS

| | | | |
|---|---|---|---|
| 2002/0197724 A1* | 12/2002 | Noronha et al. | 436/95 |
| 2004/0113124 A1* | 6/2004 | Christou et al. | 252/301.16 |
| 2004/0220298 A1* | 11/2004 | Kozee et al. | 523/160 |
| 2005/0186443 A1* | 8/2005 | Marrocco et al. | 428/690 |
| 2005/0261264 A1* | 11/2005 | Yanagida et al. | 514/184 |
| 2006/0014045 A1* | 1/2006 | Einhorn et al. | 428/690 |
| 2006/0286407 A1* | 12/2006 | Amano et al. | 428/690 |
| 2007/0122653 A1* | 5/2007 | Breuning et al. | 428/690 |
| 2007/0166836 A1* | 7/2007 | Manseki et al. | 436/518 |
| 2008/0246003 A1* | 10/2008 | Riman et al. | 252/301.4 H |
| 2008/0274028 A1* | 11/2008 | Lin et al. | 423/263 |
| 2008/0287583 A1* | 11/2008 | Mataki et al. | 524/403 |
| 2009/0000509 A1* | 1/2009 | Potrawa et al. | 106/31.13 |

OTHER PUBLICATIONS

Cai et al., 'Controlled Assembly of Dinuclear Metallorings into 1 D Coordination Polymer and Mixed-metal Rare Earth Complexes with Red-to-Green Luminescence Properties', 2004, Chemistry Letters, vol. 33, pp. 342-343.*

Kerbellec et al., "An Unprecedented Family of Lanthanide-Containing Coordination Polymers with Highly Tunable Emission Properties", published on the web, Mar. 5, 2009, Inorg. Chem. 2009, 48, pp. 2837-2843.*

* cited by examiner

Light spectra of compounds $Ln_2(C_8O_4H_2)_3(H_2O)_4$ with $Ln = Dy$, Tb or Eu

PROCESS FOR LABELING MATERIALS BASED ON ORGANIC THERMOPLASTIC OR THERMOSETTING POLYMER MATRICES

CROSS REFERENCE TO RELATED APPLICATION

This application claims priority to "Process for Labelling Materials Based on Organic Thermoplastic or Thermosetting Polymer Matrices," having serial number PCT/EP2008/056904, filed on Jun. 4, 2008. This application also claims priority to and benefit of French Application No. 0704024, filed on Jun. 6, 2007, which is incorporated by reference in its entirety.

This invention relates to the labeling of materials based on organic thermoplastic or thermosetting polymer matrices.

More specifically, this invention relates to a process for labeling such materials enabling them to be optically identified.

Materials based on organic thermoplastic or thermosetting polymer matrices are widely used to produce large numbers of articles, in particular industrial articles, of which it is often desirable to be capable of subsequently determining the origin and/or authenticity. Such identification is necessary in particular for organizing the traceability of such articles or for distinguishing possible counterfeit articles.

Counterfeiting is a major problem for numerous industries, causing them considerable loss of revenues. A very large number of economic fields are affected by this scourge. Aside from the luxury goods industry and the cosmetics industry, traditionally targeted by counterfeiters, this activity now also affects fields as varied as the automobile industry, the pharmaceutical industry and the food industry. These counterfeits can thus present problems of safety and public health.

Numerous industries are therefore searching for effective processes for labeling products that they place on the market and/or packagings used to package them. This demand is especially important for materials made from thermoplastic or thermosetting polymer matrices, which constitute the basic materials of numerous articles and substances.

In the prior art, numerous material labeling processes are known.

The safest process implement in particular holograms printed on the products to be labeled or special inks. Certain processes also implement labeling using DNA. These techniques however involve high implementation costs and can therefore be used only for products with a high added value. For many mass products made of various types of plastic materials, the use of these techniques is not however economically possible.

There are simpler and less costly techniques for labeling products, in particular techniques implementing labeling using different chemical substances. Unfortunately, these techniques are much less reliable insofar as the molecules or chemical systems implemented can be relatively easily identified by the counterfeiters, who now often take advantage of considerable means, and then copied.

This invention is therefore intended to propose a process for labeling materials based on organic thermoplastic or thermosetting matrices.

Another objective of this invention is to propose such a process that is simple to implement.

Yet another objective of this invention is to describe such a process that is inexpensive.

Another objective of the invention is to propose such a process implementing labeling compounds of which the insertion into the host matrix does not modify the properties of same.

An objective of this invention is thus to propose such a process implementing labeling compounds chemically inert enough with respect to the matrix that their introduction therein does not present a problem of compatibility with same.

Another objective of this invention is to describe such a process for easily and rapidly changing labeling, i.e. capable of implementing a very large number of labeling compounds that are structurally very similar but having easily distinguishable optical signatures, so as to allow distinguished labeling of articles and substances made of said materials based on organic thermoplastic or thermosetting matrices constituting them, according, for example to the production batch, the manufacturing date, the client or the intended use.

Yet another objective of the invention is to disclose such a method that implements compounds that are invisible to the naked eye, once inserted into the matrix.

These objectives, as well as others which will appear below, are achieved by the invention, which relates to a process for labeling a material based on at least one organic thermoplastic or thermosetting polymer matrix including a step consisting of incorporating, by dispersion during the production or shaping thereof, at least one compound based on at least one photoluminescent rare earth element according to a concentration making said compound detectable under UV irradiation, in which said compound is a coordination polymer in the form of a crystallite obtained by reacting at least one photoluminescent rare earth ion with at least one unsaturated organic ligand.

According to such a process, the labeling compounds consist of crystallites based on at least one photoluminescent rare earth element, simply dispersed in the organic matrix on which the material is based. Such a dispersion does not involve any chemical, ionic or covalent interaction with the matrix itself and does not lead to any modification of the spectrophotometric properties of said crystallites or any significant modification of the physicochemical properties of the matrix.

Also according to the invention, the coordination polymers forming such crystallites can each contain one, two, three, four, and up to thirteen distinct types of rare earth elements. It is thus possible to produce more than one million different crystallites each having a different spectrophotometric signature (for excitation at a given wavelength) but also having the same thermal and chemical properties. Therefore, there are many labeling compounds that can be used in this invention, and they can therefore be regularly or randomly changed, thereby making the copying of the labeled materials almost impossible for counterfeiters.

Such labeling compounds based on at least one photoluminescent rare earth element are therefore tracers enabling any material based on a organic thermoplastic or thermosetting polymer matrix to be labeled and enabling the subsequent identification of said material even after it has been used for a very long time.

Such compounds are sufficiently photoluminescent under UV to be capable of being used in very small concentrations in order to be detected, by spectrophotometry or, for some, as the case may be, even with the naked eye. The ability to detect photoluminescence under UV with the naked eye enables the cost of identification of products labeled according to the process of the invention to be limited considerably. The use of such tracers in very small amounts also enables the properties, in particular rheological, mechanical or thermal properties of the material thus labeled, not to be modified.

The excitation wavelength of the UV radiation used capable of revealing the presence of crystallites in the material labeled according to the process of the invention can be carefully chosen according to the absorption wavelength of the unsaturated ligand used in the composition of the crystallite considered. In particular when this ligand includes a π conjugated system, the excitation wavelength will preferably be chosen according to the absorption wavelength thereof.

Such compounds are also sufficiently chemically inert so that their introduction into the matrix does not present any problem of compatibility with other compounds present in the organic matrix-based materials, in particular such as dyes and more generally any type of adjuvant.

Moreover, these compounds are easy to identify in a routine check, since they are photoluminescent under UV irradiation.

Finally, they have the advantage of being invisible in the absence of UV radiation, once included in the material.

Rare earth elements are, contrary to their name, fairly widespread in the Earth's crust, like base metals. They are usually present simultaneously in minerals such as bastnasite, monazite, loparite (niobiotitanate), apatite, xenotime (orthophosphate) and lateritic clays.

In their elemental state, rare earth elements have a metallic appearance and are fairly soft, malleable and ductile.

The electronic transitions for rare earth elements are between discrete levels and this results in absorptions and emissions of light with a highly monochromatic nature.

In the field of absorption, certain trivalent rare earth elements enable very specific colorings to be obtained, which are profitably used in the glass and ceramics industries in which rare earth elements are used to produce pigments.

With regard to emission, applications have been developed in association with the industrial availability of rare earth elements with sufficient purities: color television, fluorescent lighting and medical radiography. A wide variety of emissions can be obtained according to the nature of the rare earth element used and the respective positions of the excited or fundamental energy levels. According to the rare earth element chosen, the light emission is located in the near ultraviolet (with cerium), the visible (red with europium, orange with samarium, green with terbium, yellow with dysprosium, blue with thulium), or the near infrared (with neodymium or erbium).

The invention can be implemented in order to label many types of materials based on thermoplastic or thermosetting polymer matrices. In particular, the invention can be used to label adhesives, in particular those used to attach labels on any type of product. The identification of the crystallite or crystallites contained in such adhesives, and, as a corollary, the product associated with said label, may be performed either by detaching said label from the product on which it is attached or by using a label made of a material transparent to UV.

These objectives are achieved by the invention, which relates to a process for labeling a material based on at least one organic thermoplastic or thermosetting polymer matrix including a step consisting of incorporating, by dispersion during the production or shaping thereof, at least one compound based on at least one photoluminescent rare earth element according to a concentration making said compound detectable under UV irradiation, in which said compound is a coordination polymer in the form of a crystallite obtained by reacting at least one photoluminescent rare earth ion with at least one unsaturated organic ligand.

According to an alternative, the process in question includes a preliminary step consisting of bringing said matrix to a temperature equal to or greater than its melting temperature, and a step consisting of mixing a predetermined amount of said at least one crystallite in said melting matrix so as to disperse it therein.

Also according to an alternative, complementary to or instead of the alternative according to the paragraph above, the process includes a step consisting of causing the dispersion of a predetermined amount of said at least one crystallite in said organic matrix under a pressure greater than the atmospheric pressure.

Preferably, the process includes a step consisting of placing said labeled material under UV radiation with an excitation wavelength suitable for the identification of said at least one crystallite incorporated therein.

Advantageously, said luminescent rare earth element is chosen from the group consisting of cerium (Ce), praseodymium (Pr), neodymium (Nd), samarium (Sm), europium (Eu), terbium (Tb), dysprosium (Dy), holmium (Ho), erbium (Er) and thulium (Tm).

Preferably, among all, said photoluminescent rare earth element is chosen from the group consisting of europium (Eu), terbium (Tb), samarium (Sm), dysprosium (Dy) and thulium (Tm).

According to an alternative of the invention, said crystallite is obtained by reacting at least one photoluminescent rare earth ion and at least one rare earth ion that is non-photoluminescent under UV with at least one unsaturated organic ligand. Said at least one non-photoluminescent rare earth element will make it possible to act as a "spacer" for the optically active rare earth elements.

Advantageously, said rare earth element that is non-photoluminescent under UV will be chosen from the group consisting of scandium (Sc), yttrium (Y), lanthanum (La) and gadolinium (Gd).

Preferably, said unsaturated ligand is chosen from the group consisting of phthalate, isophthalate, terephthalate, trimesate, trimellitate, pyromellitate and mellitate ions.

According to a preferred alternative of this invention, said at least one crystallite is included in said material based on at least one organic thermoplastic or thermosetting polymer matrix in an amount of 1 ppm to 1% by weight.

Also according to a preferred alternative of the invention, said organic thermoplastic matrix is chosen from the group consisting of polyurethane, polyethylene, polyethylene glycol, polystyrene, polyesters, polyamides, polycarbonates, polyoxomethylene, acrylonitrile-butadiene-styrene and polypropylene.

Also according to a preferred alternative of the invention, said organic thermosetting matrix is chosen from the group consisting of epoxy resins, polyvinyl acetates and acrylates.

According to an alternative of the invention, said material based on at least one organic thermoplastic or thermosetting polymer matrix includes at least one adjuvant such as a dye.

Also according to an alternative of the invention, said material based on at least one organic thermoplastic or thermosetting polymer matrix is an adhesive.

According to a preferred aspect of the invention, the process according to the invention is implemented in order to label at least two copies of the same material based on the same organic thermoplastic or thermosetting polymer matrix, and characterized in that it includes a step consisting of incorporating, by dispersion in each of said copies of said material during the production or shaping thereof:

a so-called first type of compound, based on at least two rare earth elements according to a concentration making said compound detectable under UV irradiation in said material, in which said so-called first type of compound is a coordination polymer in the form of a crystallite obtained by reacting at least two distinct rare earth elements of which at least one is photoluminescent with at least one unsaturated organic ligand, and the proportions of the rare earth elements in said compound are distinct for each of said copies; and/or a mixture of at least two compounds of a so-called second type, each based on at least one distinct rare earth element, in which said mixture of compounds can be detected under UV irradiation in said material, each so-called second type of compound of said mixture is a coordination polymer in the form of a crystallite obtained by reacting at least one rare earth element with at least one unsaturated organic ligand, at least one of the rare earth elements of said at least two compounds of the second type is a photoluminescent rare earth element, and the proportions of said compounds of the second type in said mixture are distinct for each of said copies.

In such a case, each of said compounds of the so-called first type advantageously has at least 3 distinct rare earth elements, preferably between 3 and 13 distinct rare earth elements and/or each of said compounds of the so-called second type has at least 2 distinct rare earth elements, and preferably between 2 and 13 distinct rare earth elements.

Advantageously, the process according to the invention includes a step consisting of placing the labeled material under UV radiation with an excitation wavelength chosen according to the absorption wavelength of said unsaturated ligand.

The invention also covers any material based on at least one organic thermoplastic or thermosetting polymer matrix labeled by the labeling process according to any one of claims, characterized in that it includes at least one photoluminescent labeler consisting of a compound based on at least one photoluminescent rare earth element according to a concentration making said compound detectable under UV irradiation, and said compound is a coordination polymer in the form of a crystallite obtained by reacting at least one photoluminescent rare earth ion with at least one unsaturated organic ligand.

The features and advantages of the invention will become clearer in view of the description of embodiments of the invention provided in reference to the drawings, in which.

1) PRODUCTION OF DIFFERENT CRYSTALLITES BASED ON A SINGLE RARE EARTH ELEMENT

Compounds with the general chemical formula $Ln_2[TER]_3.4H_2O$ were produced, in which formula:

Ln is europium, terbium or dysprosium, and "TER" is a terephthalate(benzene-1,4-dicarboxylate) radical.

These compounds are coordination polymers that are in the form of crystallites.

They were obtained by placing an aqueous solution of a rare earth salt in the direct presence of an aqueous solution of a terephthalic acid salt ($H_2TER$) according to the following procedure:

1 mmol of hydrated rare earth chloride ($LnCl_3.nH_2O$) is dissolved in 20 ml of water;

1.5 mmol of sodium terephthalate ($Na_2TER$) is dissolved in 20 ml of water;

two clear solutions are mixed and kept under agitation at room temperature for 10 minutes; the precipitation of a microcrystalline white solid begins instantaneously when the two solutions are placed in the presence of one another and continues for the 10 minutes of agitation;

the white precipitate is filtered, washed in water and dried in air.

The solids obtained, which are insoluble in water and in most organic solvents, can be characterized by X-ray diffraction on powder. All of these compounds are isostructural. As an example, the solid obtained with terbium crystallizes in the triclinic system (space group P-1) with the following crystalline parameters: a=6.1420(2)Å, b=10.06964(1)Å, c=10.0956(3)Å, $\alpha$=102.247(2)°, $\beta$=91.118(1)°, $\gamma$=101.518(2)° and Z=2.

The efficiency of the reaction is on the order of 80%.

The crystallites obtained have a homogeneous sub-micronic size and a platelet morphology.

The chemical stability of these compounds is also good insofar as the lanthanide ions have an excellent affinity for the carboxylate groups of the ligands.

Thus, once formed, these compounds are not very sensitive to washing with acid or basic solutions.

They are moreover stable in air for over one year.

These compounds also have good thermal stability since tests have shown that their molecular edifice was not destroyed at 500° C., i.e. they are resistant to temperatures much higher than the temperatures of use.

These compounds emit in the visible under ultraviolet irradiation. The emission can be visible to the naked eye or observed by spectrophotometry.

The mechanism of this phenomenon is known as the antenna effect. Indeed, irradiation in the UV is performed at between 254 nm and 312 nm, for example, adsorption wavelengths of organic π systems such as those existing in benzene polycarboxylate ligands.

The excitation energy is absorbed by the ligand and transferred by non-radiative transfer to the rare earth ion, which becomes de-excited as it emits in the visible.

Figure 1:
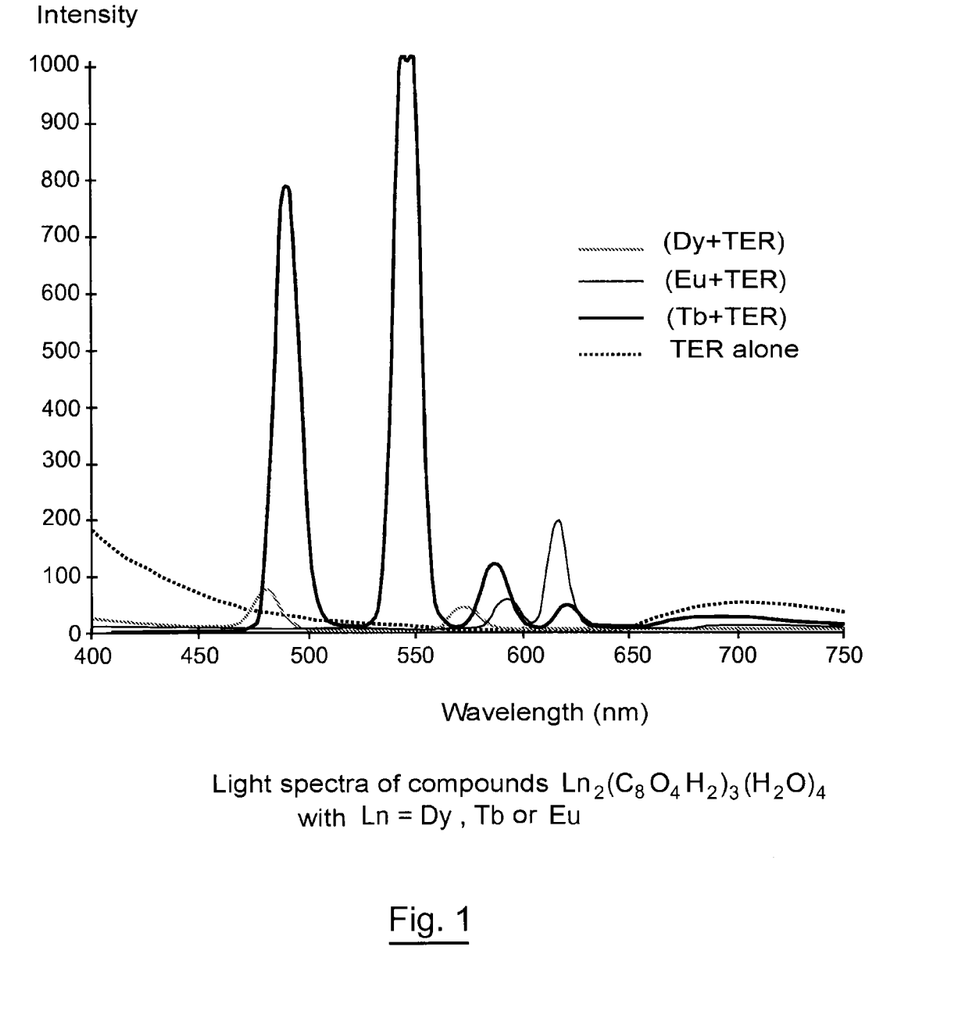
FIG. 1 shows the light spectra of different monometallic crystallites obtained with a terephthalate ligand, capable of being used in the process according to this invention.

The light spectra observed with the compounds of formulas $Ln_2[TER]_3.4H_2O$ in which Ln is dysprosium, terbium or europium are shown in FIG. 1.

The quantum efficiencies ($\phi$) of the compounds of formulas $Ln_2[TER]_3.4H_2O$ in which Ln is europium, terbium or dysprosium were determined for the solid samples using an integration sphere by the method of M. Wrighton in table 1 below.

TABLE 1

| Products | φ [%] |
|---|---|
| $Eu_2[TER]_3 \cdot 4H_2O$ | (8.8 ± 0.7) |
| $Tb_2[TER]_3 \cdot 4H_2O$ | (43.1 ± 1.6) |
| $Dy_2[TER]_3 \cdot 4H_2O$ | (0.062 ± 0.004) |

The compounds based on $Tb^{3+}$ or $Eu^{3+}$ ions have the best quantum efficiencies for industrial use.

According to procedures similar to those described above, compounds were also produced with other ligands, namely:
- the pyromellitate ion to obtain a compound of formulas $Ln_2[PYRMA]_3 \cdot nH_2O$, in which PYRMA is a pyromellitate radical (benzene-1,2,4,5-tetracarboxylate);
- the trimesate ion to obtain a compound of formulas $Ln_2[TMA]_3 \cdot 8,5H_2O$, in which TMA is a radical (benzene-1,3,5-tricarboxylate).

Figure 2:
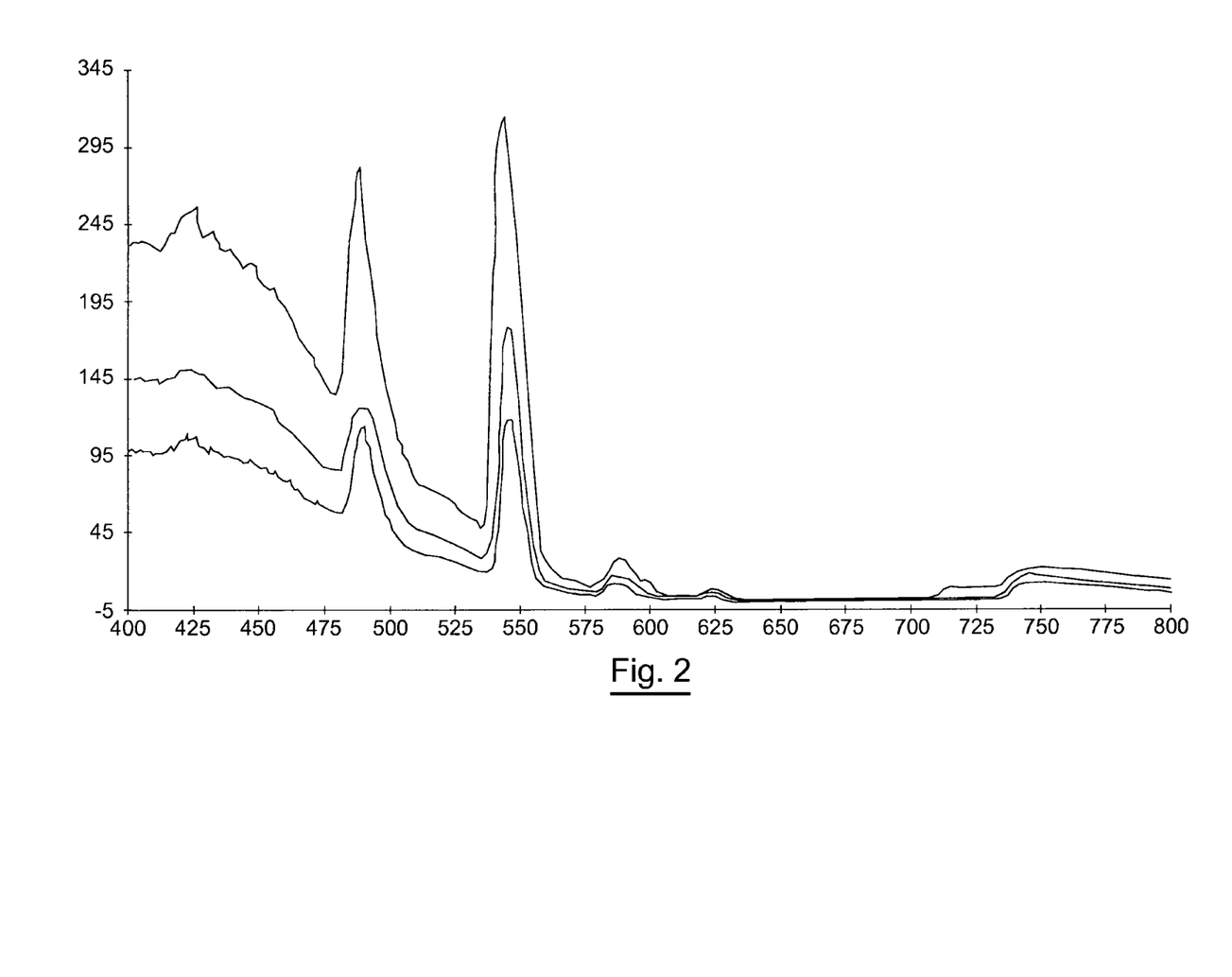
FIG. 2 shows the light spectra of different monometallic crystallites obtained with terephthalate, pyromellitate and trimesate ligands.

These compounds have different emission spectra according to the ligands used as shown in FIG. 2.

2) PRODUCTION OF CRYSTALLITES BASED ON TWO DISTINCT RARE EARTH ELEMENTS

Binary Systems

Hetero-bi-metallic crystallites based on europium and terbium and terephthalate were also produced, with the general chemical formula:

$$Tb_xEu_y(C_8O_4H_4)_3(H_2O)_4 \text{ with } x+y=2$$

In the synthesis of these bi-metallic compounds, a procedure similar to that described above for the monometallic compounds was used, but by varying the molar ratios of the rare earth salts used so as to obtain crystallites having variable proportions of europium and terbium.

In consideration of the low concentrations in which the crystallites are used in the process according to the invention, it was verified that each crystallite contains the same relative proportions of Tb and Eu as the general powder. It is indeed important that each crystallite contains all of the information. This was verified by microanalysis using a scanning electron microscope (SEM). The results of this analysis appear in table 2 below and unambiguously confirm the possibility of producing powders in which relative proportions of Tb and Eu are perfectly controllable at the crystallite scale.

TABLE 2

| Molar percentages of the starting solutions | | Analysis of crystallites by scanning microscopy | |
|---|---|---|---|
| % Terbium | % Europium | % Terbium | % Europium |
| 10 | 90 | 12 (2) | 87 (2) |
| 20 | 80 | 20 (2) | 79 (2) |
| 30 | 70 | 28 (2) | 71 (2) |
| 40 | 60 | 39 (2) | 60 (2) |
| 50 | 50 | 50 (2) | 49 (2) |
| 60 | 40 | 60 (2) | 39 (2) |
| 80 | 20 | 80 (2) | 19 (2) |
| 90 | 10 | 89 (2) | 10 (2) |

According to the relative percentages of each of the rare earth elements in the crystallites, a chromatic variation is observed with the naked eye as well as with the fluorometer.

Figure 3:
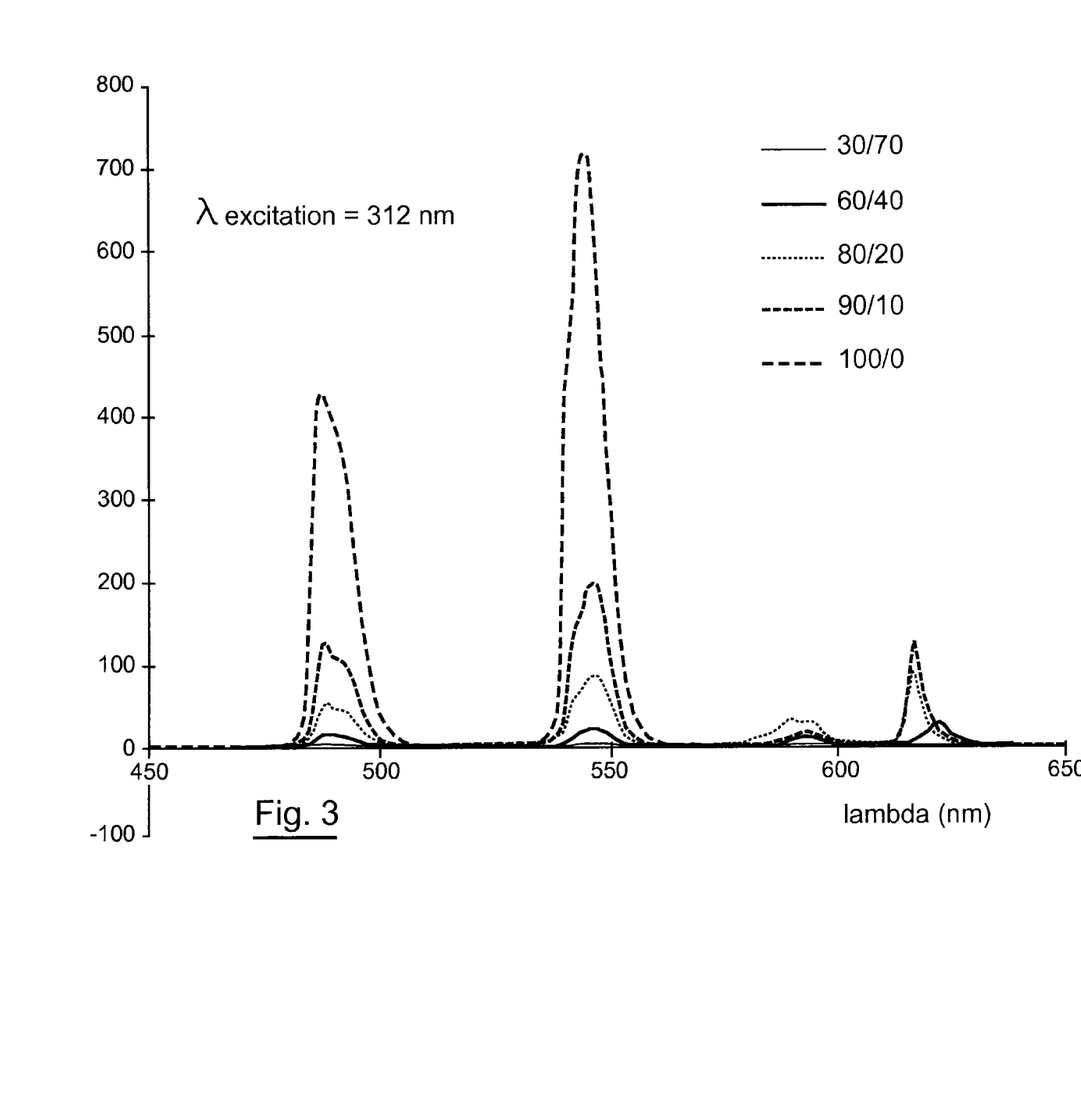
FIG. 3 shows the light spectra of different bimetallic crystallites capable of being used in the process according to this invention.

This is confirmed by FIG. 3, which shows fluorescence spectra obtained with these different compounds.

3) PRODUCTION OF CRYSTALLITES BASED ON THREE DISTINCT RARE EARTH ELEMENTS

Tertiary System

A) A hetero-tri-metallic crystallite based on cerium, europium, terbium and terephthalate with the molar formula: $Ce_{0.15}Eu_{0.15}Tb_{1.7}[Ter]_3 \cdot 4H_2O$ was also produced, corresponding to the following molar proportions of rare earth elements: $Ce_{7.5}Eu_{7.5}Tb_{85}$.

In a first step, 3 equivalents of the sodium salt of 1,4-benzenedicarboxylic acid are dissolved in 35 mL of distilled water. 0.15 equivalents of $EuCl_3 \cdot nH_2O$ are dissolved in 15 mL of distilled water, 0.15 equivalents of $CeCl_3 \cdot nH_2O$ are dissolved in 15 mL of distilled water and 1.7 equivalents of $TbCl_3 \cdot nH_2O$ are dissolved in 15 mL of distilled water. The three solutions are kept under magnetic agitation for 5 minutes. The three solutions containing the rare earth elements are then mixed. The mixture is left for 5 minutes under magnetic agitation, then the solution containing the terephthalate ligand is added to it. A white precipitate immediately forms. The solution is kept under agitation for 15 minutes. The precipitate thus obtained is filtered and dried in the open air. The efficiency of this synthesis is on the order of 95%.

Figure 4:
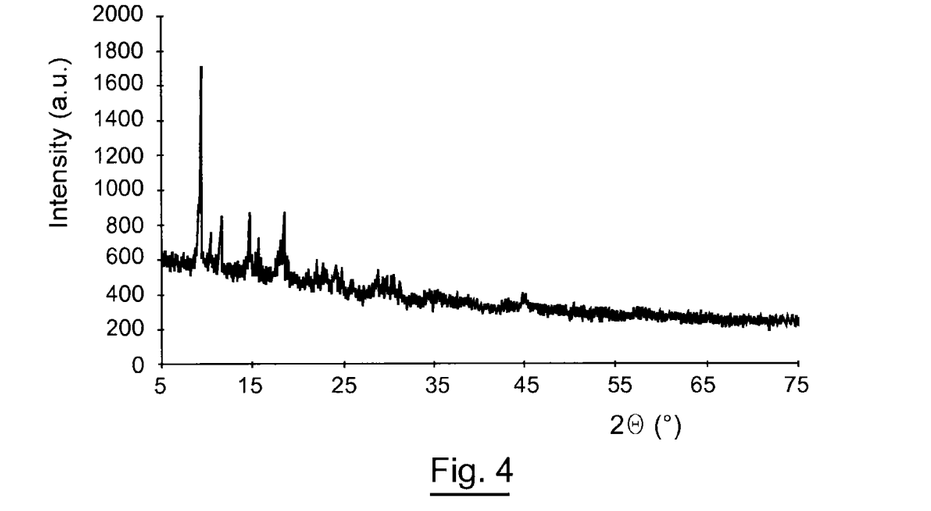
FIG. 4 shows the X-ray diffraction pattern of a crystallite capable of being used in this invention and having 2 distinct rare earth ions.

The homogeneity of the microcrystalline powder was verified by SEM microanalyses and by X-ray diffraction on powder. The diagram according to FIG. 4 proves that there is indeed only one mixed trimetallic phase and not a mixture of three monometallic phases.

A spectroscopic characterization of this hetero-tri-metallic compound was performed under the following recording conditions:

Excitation wavelength: 312 nm (corresponding to the maximum absorption wavelength of the system it of the terephthalate ligand).

Figure 5:
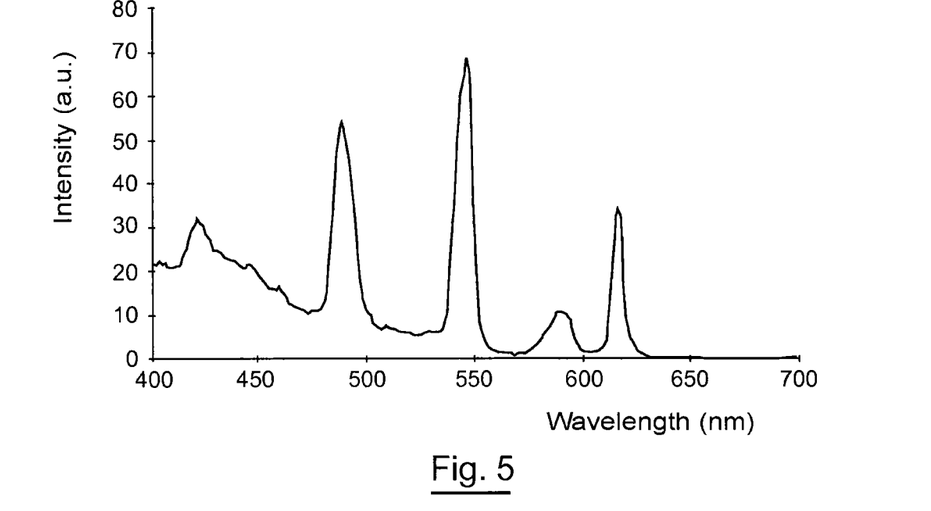
FIG. 5 shows the light spectrum of the crystallite of which the diffraction pattern is shown in FIG. 4.

Excitation slot width: 5 nm
Emission slot width: 5 nm
Scanning speed: 200 nm/min The light spectrum in FIG. 5 shows the rays characteristic of the terbium (III) and europium (III) ions.

The emission wavelengths characteristic of europium are centered around 594 nm and 617 nm, according to the following indexing:

| Transitions | Emission wavelength |
|---|---|
| $^5D_0 \rightarrow {}^7F_1$ | 594 nm |
| $^5D_0 \rightarrow {}^7F_2$ | 617 nm |

The emission wavelengths characteristic of terbium are centered around 488 nm, 546 nm, 589 nm and 622 nm, according to the following indexing:

| Transitions | Emission wavelength |
|---|---|
| $^5D_4 \rightarrow {}^7F_6$ | 488 nm |
| $^5D_4 \rightarrow {}^7F_5$ | 546 nm |
| $^5D_4 \rightarrow {}^7F_4$ | 589 nm |
| $^5D_4 \rightarrow {}^7F_3$ | 622 nm |

B) Another hetero-tri-metallic crystallite based on cerium, europium, terbium and terephthalate was also produced with a molar formula very similar to the corresponding to the following molar proportions of rare earth elements: $Ce_{10}Eu_{2.5}Tb_{87.5}$.

In a first step, 3 equivalents of the sodium salt of 1,4-benzenedicarboxylic acid are dissolved in 35 mL of distilled water. 0.05 equivalents of $EuCl_3.nH_2O$ are dissolved in 15 mL of distilled water, 0.2 equivalents of $CeCl_3.nH_2O$ are dissolved in 15 mL of distilled water and 1.75 equivalents of $TbCl_3.nH_2O$ are dissolved in 15 mL of distilled water. The three solutions are kept under magnetic agitation for 5 minutes. The three solutions containing the rare earth elements are then mixed. The mixture is left for 5 minutes under magnetic agitation, then the solution containing the ligand is added to it. A white precipitate immediately forms. The solution is kept under agitation for 15 minutes. The precipitate thus obtained is filtered and dried in the open air. The efficiency of this synthesis is on the order of 95%.

Figure 6:
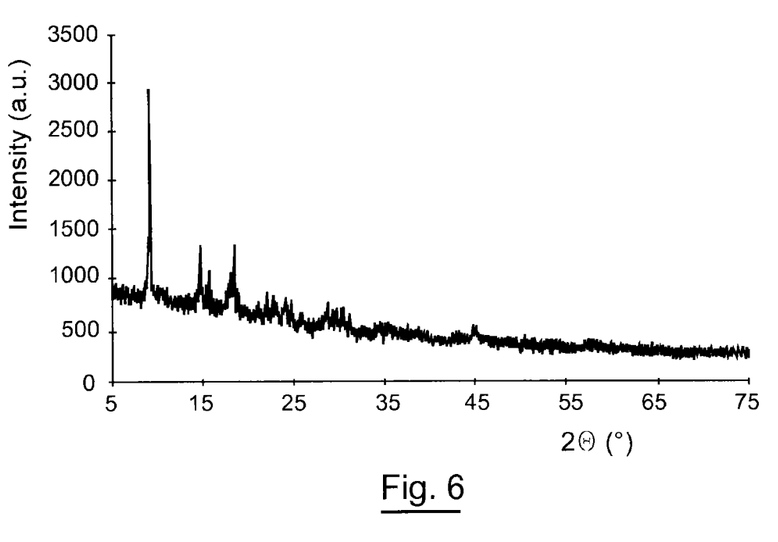
FIG. 6 shows the X-ray diffraction pattern of another crystallite capable of being used in this invention and having the same 2 rare earth ions but in different molar proportions.

The homogeneity of the microcrystalline powder was verified by SEM microanalyses and by X-ray diffraction on powder. The diagram according to FIG. 6 proves that there is indeed only one mixed trimetallic phase and not a mixture of three monometallic phases.

A spectroscopic characterization of this hetero-tri-metallic compound was performed under the same recording conditions as in example A) above.

Figure 7:
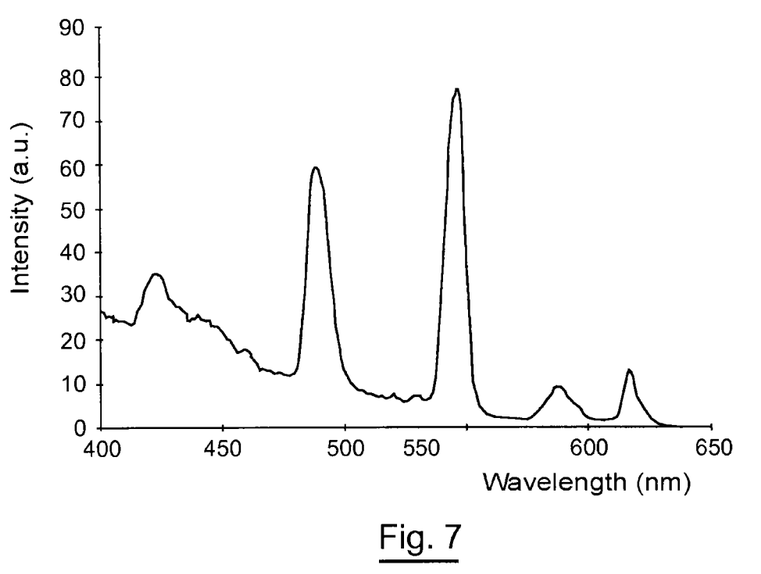
FIG. 7 shows the light spectrum of the crystallite of which the diffraction pattern is shown in FIG. 6.

The light spectrum in FIG. 7 shows the rays characteristic of the terbium (III) and europium (III) ions. The emission wavelengths characteristic of europium are centered around 594 nm and 617 nm, and those characteristic of terbium are centered at 488 nm, 546 nm, 589 nm and 622 nm, according to the same indexings as those mentioned above. However, this spectrum shows differences in terms of relative intensities of the different peaks with the spectrum according to FIG. 5, enabling this crystallite to be distinguished from that according to example A.

4) PRODUCTION OF A CRYSTALLITE BASED ON FOUR DISTINCT RARE EARTH ELEMENTS

Quaternary System

A hetero-tetra-metallic crystallite based on yttrium, dysprosium, europium, terbium and terephthalate was also produced with the molar formula: $Y_{1.20}Dy_{0.52}Tb_{0.08}Eu_{0.20}[Ter]_3.4H_2O$ corresponding to the following molar proportions of rare earth elements: $Y_{60}Dy_{26}Tb_4Eu_{10}$.

In a first step, 3 equivalents of the sodium salt of 1,4-benzenedicarboxylic acid are dissolved in 35 mL of distilled water. 1.2 equivalents of $YCl_3.nH_2O$ are dissolved in 15 mL of distilled water, 0.52 equivalents of $DyCl_3.nH_2O$ are dissolved in 15 mL of distilled water, 0.08 equivalents of $TbCl_3.nH_2O$ are dissolved in 15 mL of distilled water and 0.20 equivalents of $EuCl_3.nH_2O$ are dissolved in 15 mL of distilled water. The four solutions are kept under magnetic agitation for 5 minutes. The four solutions containing the rare earth elements are then mixed. The mixture is left for 5 minutes under magnetic agitation, then the solution containing the ligand is added to it. A white precipitate immediately forms. The solution is kept under agitation for 15 minutes. The precipitate thus obtained is filtered and dried in the open air. The efficiency of this synthesis is on the order of 95%.

Figure 8:
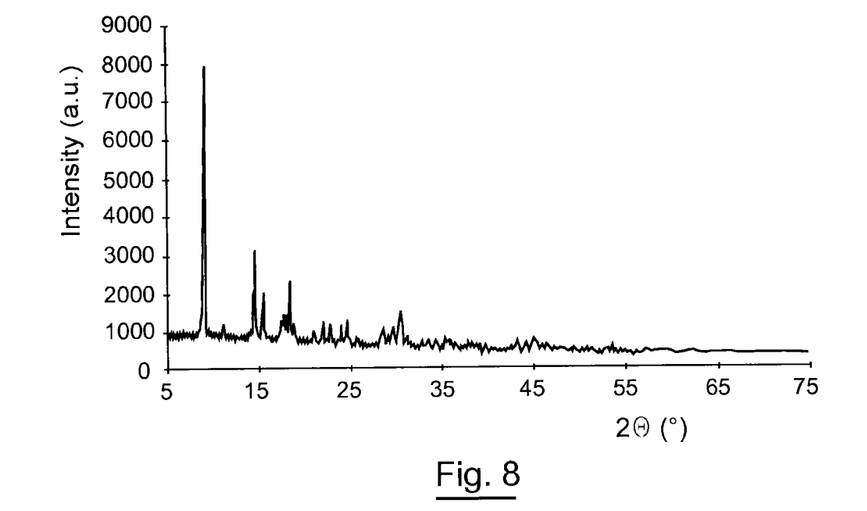
FIG. 8 shows the X-ray diffraction pattern of a crystallite capable of being used in this invention and simultaneously having 4 rare earth ions.

The homogeneity of the microcrystalline powder was verified by SEM microanalyses and by X-ray diffraction on powder. The diagram according to FIG. 8 proves that there is indeed only one mixed tetra-metallic phase and not a mixture of four monometallic phases.

Figure 9:
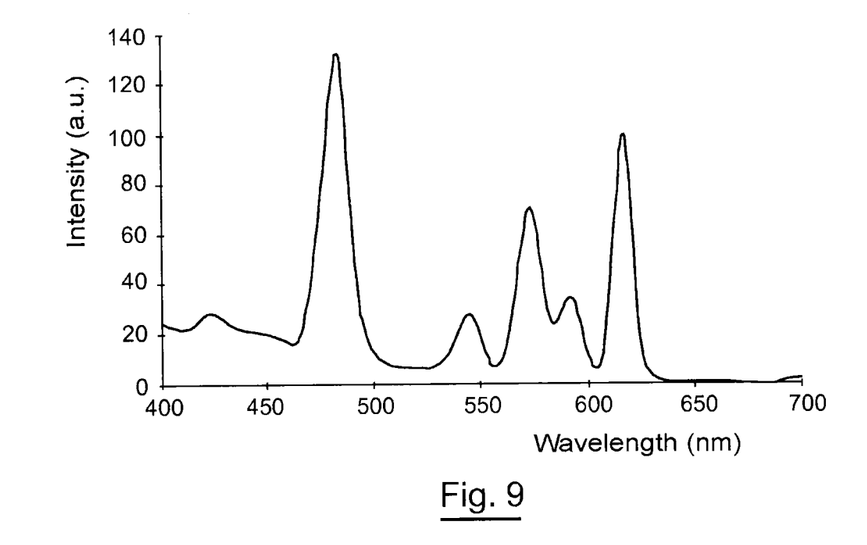
FIG. 9 shows the light spectrum of the crystallite of which the diffraction pattern is shown in FIG. 8.

A spectroscopic characterization of this hetero-tetra-metallic compound was performed under the same recording conditions as in examples A) and B) above. The light spectrum in FIG. 9 shows the rays characteristic of the terbium (III) and europium (III) and dysprosium (III) ions. The emission wavelengths characteristic of europium are centered around 594 nm and 617 nm, those characteristic of terbium are centered at 488 nm, 546 nm, 589 nm and 622 nm, according to the same indexings as those mentioned above; and finally those characteristic of dysprosium are centered at 482 nm and 574 nm according to the following indexing:

| Transitions | Emission wavelength |
| --- | --- |
| $^4D_{9/2} \rightarrow {}^6F_{15/2}$ | 482 nm |
| $^4D_{9/2} \rightarrow {}^6F_{13/2}$ | 574 nm |

The non-photoluminescent yttrium (III) ions enable the optically active terbium (III), europium (III) and dysprosium (III) ions to be better isolated from one another and thus act as "spacers".

5) PRODUCTION OF A CRYSTALLITE BASED ON THIRTEEN DISTINCT RARE EARTH ELEMENTS

A crystallite containing, in equivalent weight proportions, the following thirteen rare earth elements: lanthanum, cerium, praseodymium, neodymium, samarium, europium, gadolinium, terbium, dysprosium, holmium, erbium, thulium and yttrium, was also produced.

Figure 10:
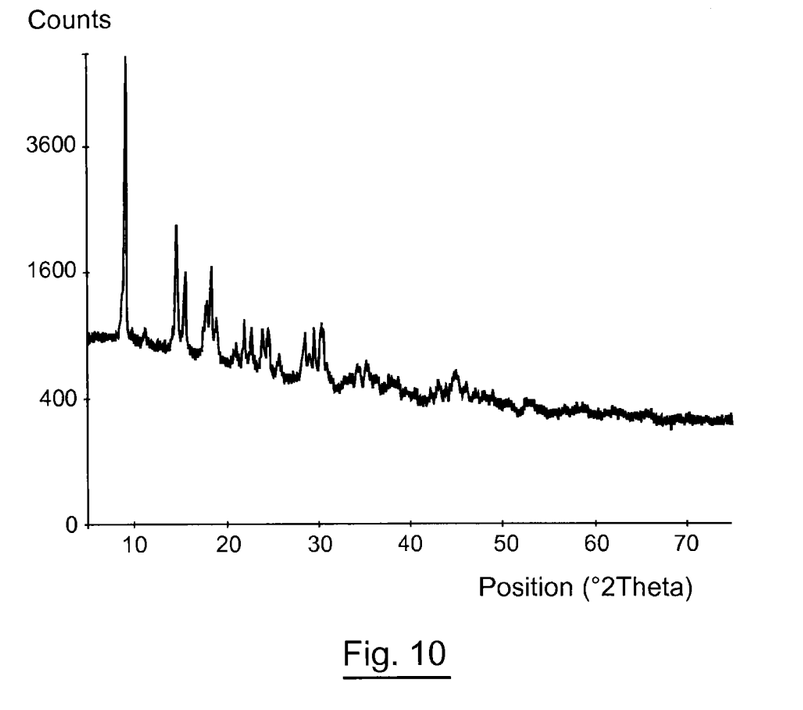
FIG. 10 shows the X-ray diffraction pattern of a crystallite capable of being used in this invention and simultaneously having 13 distinct rare earth ions.

The homogeneity of the microcrystalline powder was verified by SEM microanalyses and by X-ray diffraction on powder. The diagram according to FIG. 10 proves that there is indeed only one mixed multi-metallic phase and not a mixture of thirteen monometallic phases.

6) PRODUCTION MATERIALS BASED ON ORGANIC THERMOPLASTIC OR THERMOSETTING MATRICES INTEGRATING CRYSTALLITES BASED ON LUMINESCENT RARE EARTH ELEMENTS

In a first test, the crystallite of formulation $Tb_2[TER]_3(H_2O)_4$ was included in the amount of a weight concentration of 0.1% in a material consisting of polyurethane.

The incorporation of this crystallite in the polyurethane matrix was performed, according to the invention, by simple dispersion thereof in said matrix. This dispersion was performed by bringing the polyurethane to a temperature and a pressure enabling its extrusion in the form of a first watchband.

In a second test, the crystallite of formulation $Eu_2[TER]_3(H_2O)_4$ was included in the amount of a weight concentration of 0.1% in a material consisting of polyurethane and a black dye.

The incorporation of this crystallite in the polyurethane matrix was performed, according to the invention, by simple dispersion thereof in said matrix after a dye had been added to it.

This dispersion was performed by bringing the polyurethane to a temperature and a pressure enabling its extrusion in the form of a second watchband, which could be distinguished by the naked eye from the first watchband only by its black color.

These two tests enabled the demonstration that, aside from their difference in colors, these two articles could be distinguished from one another by subjecting them to ultraviolet irradiation. In this example, an excitation wavelength of 312 nm was used. An emission in the visible (green) was thus observed for the first band and another emission in the visible (red) was observed for the second band.

Different photoluminescence results over time also enabled the observation that the photoluminescence properties were preserved over time.

These tests also enabled the observation that the photoluminescence of the crystallites used in this invention was not disrupted by the presence of dyes.

Other tests were conducted with other types of organic matrices, in particular such as polypropylene, polyethylene, polyethylene glycol, polystyrene, and so on.

For all of these thermoplastic compounds, the same procedure was followed.

After having brought the host polymer matrix to its melting point, a small amount of photoluminescent crystallite was dispersed in the matrix.

In every case, the photoluminescent compounds used were not destroyed and preserved their photoluminescent properties.

These tests confirmed the possibility of incorporating such crystallites in processes of production or shaping of material implementing a step at high temperature and/or pressure.

In other tests, the crystallite of formulation $Tb_2[TER]_3(H_2O)_4$ and the crystallite of formulation $Eu_2[TER]_3(H_2O)_1$ were each included, in the amount of a weight concentration of 0.1% in a thermosetting adhesive consisting of an epoxy resin sold under the name Araldite (registered trademark) as well as in a polyvinyl acetate-type thermosetting adhesive sold under the name UHU (registered trademark).

The results of these different tests showed that the implementation of the process according to the invention did not involve any destruction of the crystallites during their insertion into a polymer matrix by the classic processes of extrusion and fusion. The invention can therefore be used to label systems having an organic matrix, but also all products sold under protective films or of which the packagings comprise labels, by labeling these films and/or these labels.

Other organic matrix labeling tests were performed with crystallites of formula $Ln_2[PYRMA]_3.nH_2O$ and $Ln_2[TMA]_3.8.5H_2O$, in which Ln is europium, terbium or dysprosium, PYRMA is the pyromellitate ligand (benzene-1,2,4,5-tetracarboxylate) and TMA is the trimesate ligand (benzene-1,3,5-tricarboxylate).

The results obtained are comparable to those obtained with the compounds produced from the terephthalate ligand.

Finally, other tests were conducted using the hetero-bimetallic crystallites described in A) and B) above to label different batches of the same material.

The spectrophotometric analysis of the emission of these bimetallic compounds contained in these different batches shows a variable response according to the relative concentrations of rare earth elements in the crystallites.

Such bimetallic compounds can thus be used to distinctively label different copies of the same material, thus having a benefit in particular in the labeling of different batches of the same material, in the labeling of said material according to the client to whom it is sold, in the labeling of said material according to its manufacturing date (millesimage), and in the labeling of said material in order to detect copies of same, and so on.

The easily modulable nature of the crystallites that can be used in this invention makes it almost impossible for counterfeiters to reproduce the material/dedicated crystallite.

The invention claimed is:

1. A method for labeling a material, wherein the material includes an organic thermoplastic or thermosetting polymer matrix, the method comprising:
   reacting two to ten photoluminescent rare earth ions and at least two rare earth ions that are non-photoluminescent under ultraviolet light, with one unsaturated organic ligand to form one coordination polymer in the form of a crystallite, wherein the non-photoluminescent rare earth ions are selected from the group consisting of scandium, yttrium, and lanthanum; and
   incorporating, by dispersion during the production or shaping thereof, said crystallite into said thermoplastic or thermosetting polymer matrix of the material, wherein said crystallite is included in said material in an amount of 1 ppm to 1% by weight making said crystallite detectable under UV irradiation, said dispersion comprising no chemical reaction nor ionic nor covalent interaction of the crystallite with the matrix, and said crystallite having a specific spectrophotometric signature.

2. The method according to claim 1, further comprising bringing said matrix to a temperature equal to or greater than its melting temperature, and mixing a predetermined amount of said crystallite in said melting matrix so as to disperse it therein.

3. The method according to claim 1, further comprising a preliminary step consisting of causing the dispersion of a predetermined amount of said crystallite in said organic matrix under a pressure greater than the atmospheric pressure.

4. The method according to claim 1, further comprising placing said labeled material under UV radiation with an excitation wavelength suitable for the identification of said crystallite incorporated therein.

5. The method according to claim 1, wherein said two photoluminescent rare earth elements are chosen from the group consisting of cerium (Ce), praseodymium (Pr), neodymium (Nd), samarium (Sm), europium (Eu), terbium (Tb), dysprosium (Dy), holmium (Ho), erbium (Er) and thulium (Tm).

6. The method according to claim 5, wherein said two photoluminescent rare earth elements are chosen from the group consisting of europium (Eu), terbium (Tb), samarium (Sm), dysprosium (Dy) and thulium (Tm).

7. The method according to claim 1, wherein said unsaturated ligand is chosen from the group consisting of phthalate, isophthalate, terephthalate, trimesate, trimellitate, pyromellitate and mellitate ions.

8. The method according to claim 1, wherein said organic thermoplastic matrix is chosen from the group consisting of polyurethane, polyethylene, polyethylene glycol, polystyrene, polyesters, polyamides, polycarbonates, polyoxomethylene, acrylonitrile-butadiene-styrene and polypropylene.

9. The method according to claim 1, wherein said organic thermosetting matrix is chosen from the group consisting of epoxy resins, polyvinyl acetates and acrylates.

10. The method according to claim 1, wherein said material including an organic thermoplastic or thermosetting polymer matrix includes at least one adjuvant, said adjuvant being a dye.

11. The method according to claim 1, wherein said material including an organic thermoplastic or thermosetting polymer matrix is an adhesive.

12. The method according to claim 4, further comprising placing the labeled material under UV radiation with an excitation wavelength chosen according to the absorption wavelength of said unsaturated ligand.

13. The method according to claim 1 wherein the method further comprises: identifying or tracing an article containing the labeled material by detecting the distinguishable signature of said crystallite incorporated in the material, wherein the distinguishable signature of the crystallite enables identification and tracing of articles containing the labeled material and distinguishing articles containing the material from counterfeited articles that do not contain the material with said crystallite.

* * * * *